(12) United States Patent
Zlotkin

(10) Patent No.: US 6,830,761 B1
(45) Date of Patent: Dec. 14, 2004

(54) COMPOSITION COMPRISING MICRO-ENCAPSULATED IRON

(75) Inventor: Stanley H. Zlotkin, Toronto (CA)

(73) Assignee: Ped-Med Ltd., Toronto (CA)

( * ) Notice: Subject to any disclaimer, the term of this patent is extended or adjusted under 35 U.S.C. 154(b) by 0 days.

(21) Appl. No.: 09/257,902

(22) Filed: Feb. 25, 1999

(30) Foreign Application Priority Data

Feb. 27, 1998 (CA) .............................................. 2230801

(51) Int. Cl.[7] .............................. A61K 9/16; A61K 9/50
(52) U.S. Cl. ...................... 424/490; 424/489; 424/439; 206/528
(58) Field of Search .......................... 424/76, 489, 480, 424/439, 490; 514/814; 206/528

(56) References Cited

U.S. PATENT DOCUMENTS 3,992,556 A * 11/1976 Kovacs et al. ................. 426/72

OTHER PUBLICATIONS

International Vitamin A Consultative Group, IVACG Statement, *Vitamin A and Iron Interactions*, Jun. 1998.
Alizon Draper, The Oxford Brief, *Child Development and Iron Deficiency*, May 1997.
Rebecca J. Stoltzfus, et al., *Guidlines for the Use of Iron Supplements to Prevent and Treat Iron Deficiency Anemia*, pp. 1–39.
U.S. Department of Health and Human Services, *Recommendations to Prevent and Control Iron Deficiency in the United States*, Morbidity and Mortality Weekly Report, vol. 47, No. RR, Apr. 3, 1998, pp. 1–330.
Micronutrient Initiative, *Expert Consultation on Anemia Determinants and Interventions*, Mar. 6, 1998.
Claudia Schauer et al., Home Fortification with Micronutrient Sprinkles—A New Approach for the Prevention and Treatment of ediatr Child Health, vol. 8 No. 2, Feb. 2003.
Stanley Zlotkin, "Treatment of Anemia with Microencapsulated Ferrous Fumarate Plus Ascorbic Acid Supplied as . . . ", American Society for Clinical Nutrition 2001;74:791–5.

* cited by examiner

Primary Examiner—Shelley A. Dodson
Assistant Examiner—Konata M. George

(57) ABSTRACT

A composition useful in the prevention of iron deficiency anemia is provided. The composition comprises micro-encapsulated iron granules in combination with a lipid-based excipient. The composition may additionally contain other micronutrients including ascorbic acid, zinc, vitamin A and iodine. The composition is particularly useful for the prevention of iron deficiency anemia in infants between the ages of 6 and 24 months of age since it can readily be admixed with the semi-solid foods this age group consumes.

22 Claims, 1 Drawing Sheet

COMPOSITION COMPRISING MICRO-ENCAPSULATED IRON

FIELD OF THE INVENTION

The present invention relates to micronutrient supplements. More particularly, the present invention relates to micronutrient supplements comprising iron which are especially useful for administration to infants.

BACKGROUND OF THE INVENTION

Micronutrient malnutrition may be defined as the insufficient dietary consumption of nutrients such as vitamin A, iron and iodine. It is a significant problem affecting more than 2 billion people worldwide, particularly women and children living in poverty. Iron deficiency is the most common nutritional problem in the world, affecting two thirds of children in most developing nations. Anemia resulting from iron deficiency in young children has become very common since the level of bioavailable iron in a typical infant's diet is low while their rapid growth requires a much higher level of iron. The consequences of iron deficiency anemia (IDA) are very serious as it is associated with impaired cognitive and psychomotor development, reduced growth and decreased resistance to infection.

The age group at most risk is infants 6 to 24 months of age. Infants up to 6 months of age are protected from deficiency by iron stores present at birth and iron obtained from breast milk. Children 2 years of age and older obtain bioavailable iron from a diversifying diet. For infants between the ages of 6 to 24 months, however, iron obtained from breast milk cannot sufficiently meet the needs of rapid growth, while the solid food diet of this age group is not diversified enough to provide the required iron.

Micronutrient malnutrition, and more particularly iron deficiency, can be prevented, or at least controlled, by diet diversification, food fortification and nutrient supplementation. However, these solutions cannot readily be implemented in developing countries. For example, the ability of those in developing countries to diversify their diet is dictated not only by the availability of foods with a high nutrient content, but more importantly by the cost of such foods. Iron-fortified foods are, of course, an appropriate, effective means to prevent anemia; however, the cost of these foods is prohibitive to most families living in developing countries. The solution appears to lie in the remaining alternative, iron supplements, assuming that suitable cost-effective supplements can be developed for administration to infants and young children.

Currently, iron supplements are available for administration to infants and young children in the form of a concentrated solution or syrup due to the fact that they cannot swallow tablets or pills. However, in comparison to the use of tablets or pills, use of these formulations is associated with significant disadvantages. At the outset, shipping and storage of such iron-containing formulations is more costly and these formulations have a shorter shelf-life than comparable tablets or pills. Solution formulations are also more complicated to dispense and, as a result, there exists a higher likelihood of dispensing incorrect dosages. Further, there is poor compliance with liquid formulations because of their unpleasant metallic taste. Finally, administration of iron in solution can cause stains on teeth, a disadvantage which is reversible but undesirable in the interim.

There is a need, thus, to provide a cost-effective iron supplement suitable for administration to infants and young children which is useful to prevent iron deficiency anemia.

SUMMARY OF THE INVENTION

The present invention provides a composition supplemented with iron which is particularly suitable for administration to infants, and more particularly, suitable for administration to infants and young children, i.e. children under 2 years of age.

Accordingly, in one aspect, the present invention provides a composition comprising micro-encapsulated iron granules in combination with a pharmaceutically acceptable lipid-based excipient.

In another aspect of the present invention, there is provided a method for preventing iron deficiency anemia in a mammal comprising the steps of adding a therapeutically effective amount of a composition comprising micro-encapsulated iron granules and a pharmaceutically acceptable lipid-based excipient to food and administering the food to said mammal.

In another aspect of the present invention, there is provided an article of manufacture comprising packaging material and a pharmaceutical composition contained within said packaging material, wherein said pharmaceutical composition is therapeutically effective to prevent iron deficiency anemia, and wherein the packaging material comprises a label which indicates that the composition comprises iron and that iron ingestion is effective to prevent iron deficiency anemia, said composition comprising a therapeutically effective amount of micro-encapsulated iron granules in combination with a pharmaceutically acceptable lipid-based excipient.

In yet another aspect of the present invention, there is provided an article of manufacture comprising packaging material and a pharmaceutical composition contained within said packaging material, wherein said pharmaceutical composition is therapeutically effective to prevent iron deficiency anemia, and wherein the packaging material comprises a label which indicates that the composition can bemused to prevent iron deficiency anemia, said composition comprising a therapeutically effective amount of micro-encapsulated iron granules in combination with a pharmaceutically acceptable lipid-based excipient.

The present composition advantageously provides iron in a form which is readily administrable on addition to food, requiring no further preparation prior to administration. When added to food, the composition does not adversely affect the taste or appearance of food because it is encapsulated, thereby preventing any leaching that might otherwise occur. Moreover, the provision of micro-encapsulated iron in a lipid-based excipient makes the present composition useful for administration to infants, particularly between the ages of 6–24 months, an age group which is especially vulnerable to iron deficiency. In this regard, the composition can be added directly to infant foods, including cereals, purees, formula and milk.

DETAILED DESCRIPTION OF THE INVENTION

Figure 1:
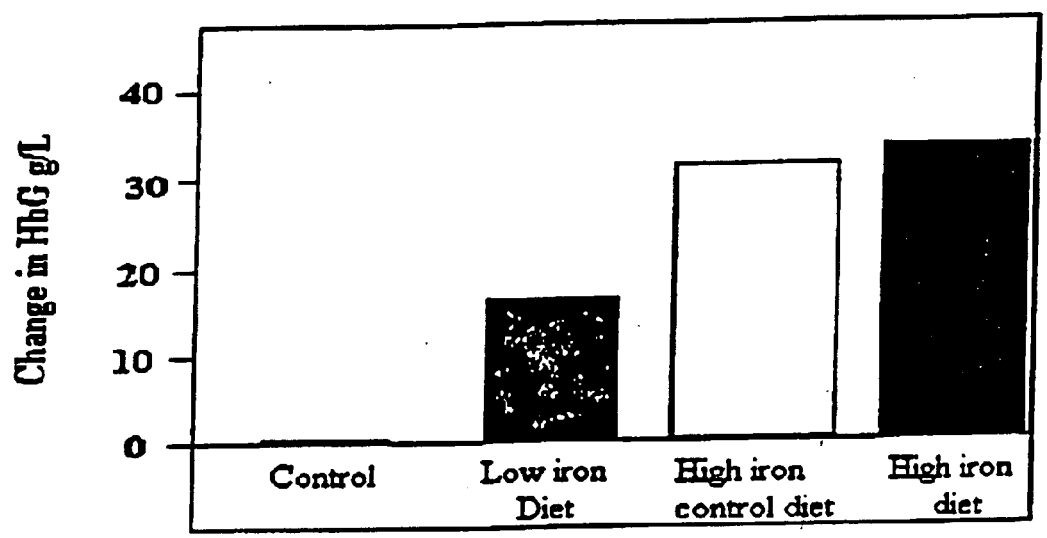
FIG. 1 is a bar graph illustrating the effect of various iron-containing compositions on hemoglobin response in rats.

The present invention provides a composition useful to prevent iron deficiency anemia comprising micro-encapsulated iron granules in combination with a pharmaceutically acceptable lipid-based excipient. The term "prevent" as it is used herein with respect to the capacity of the present composition to affect the onset of iron deficiency anemia refers not only to prevention of the disease but may also refer to prevention of one or more of the adverse effects associated with anemia.

The term "lipid-based", as it is used herein with respect to the excipient, is meant to refer to excipients which are lipids, or which comprise a lipid component. Lipid-based excipients will combine with the micro-encapsulated iron granules of the present composition in a chemically stable manner in which no adverse interaction occurs such as undesirable aesthetic changes or undesirable changes to the taste of the product. Moreover, lipid-based excipients conveniently allow combination of the composition with foods, the means by which it is administered.

The micro-encapsulated iron granules of the present composition may comprise any bioavailable solid form of iron including iron salts such as ferrous sulphate, ferrous fumarate, ferrous succinate, ferrous gluconate, ferric pyrophosphate, ferric saccharate, ferric orthophosphate or any other compound capable of providing iron with an appropriate bioavailability. Bioavailability can be determined using the standard "hemoglobin-repletion" method described in detail by Fritz et al. in the Journal of the Association of Official Analytical Chemists (AOAC), 1974, 57:513–517 and by Williams in the Official methods of analysis of the AOAC, $14^{th}$ edition, Arlington VA, AOAC, 1984, p.880–881. This method generally involves feeding anemic rats with a test iron compound and comparing their iron uptake with the iron uptake of anemic rats fed a reference compound determined to have a relative iron bioavailability of 100%. The selected iron compound is formed into granules using techniques and machinery well-known to those of skill in the art. For use in the present composition, granules are prepared having a diameter of no more than about 850 microns. Granules of this size range can be obtained, for example, using a U.S. No. 20 sieve. The granulated iron compound is provided as a fine free flowing powder.

Once formed into granules of a desired size, the iron compound is coated or encapsulated with an inert substance that will not interfere with the uptake of the iron compound. The coating functions to sustain the release of the iron, effectively masking the characteristic unpleasant taste of the iron compound, preventing discoloration of the foods to which it is added thereby providing a form of iron that can readily be added to foods. The coating also prevents the undesirable interaction between nutrients in the foods to which it is added as well as additional nutrients that may be added to the composition itself. The inert coating may be selected from a number of suitable substances including, but not limited to, mono- or di-glycerides, ethyl cellulose, hydrogenated soybean oil, acacia gun and mixtures thereof.

The encapsulated granulated iron compound is admixed with a pharmaceutically acceptable lipid-based excipient. The term "pharmaceutically acceptable" refers to an excipient acceptable for use in the pharmaceutical and veterinary arts, which is not toxic or otherwise inacceptable. Examples of suitable lipid-based excipients include mono-, di- and tri-glycerides, especially naturally extracted unsaturated edible oils in hydrogenated form (such as vegetable oil, castor oil, cottonseed oil, corn oil, canola oil, rapeseed oil, peanut oil, sesame seed oil, coconut oil and mixtures thereof).

The present composition may be supplemented with additional micronutrients. Such additional micronutrients may function to enhance the absorption of iron on administration. In a preferred embodiment of the present invention, the composition may additionally comprise ascorbic acid (vitamin C), preferably in an amount ranging from about 40–50 mg per 15 mg of elemental iron. The ascorbic acid enhances the absorption of the iron into the bloodstream, providing a more effective composition. Further, the absorption of iron is known to be enhanced in the presence of reducing compounds. Examples of reducing compounds are compounds containing sulfhydryl groups such as the amino acids, lysine and histidine. The absorption of iron is also enhanced in the presence of meat. Accordingly, the present composition can advantageously be consumed with meat. Alternatively, the present composition may additionally contain dessicated meat particles to provide enhanced iron absorption and to provide protein content that would be particularly desirable for administration to populations in which protein consumption is low, such as populations in developing countries.

Alternatively, or additionally, the present composition may be supplemented with other micronutrients, particularly those micronutrients which are typically absent from the diet or present in insufficient quantities. Examples of micronutrients that may be added to the composition include vitamin A, zinc and iodine, provided in appropriate bioavailable form. In this regard, vitamin A may be added to the present composition in the form of retinyl palmitate, zinc may be added in the form of zinc sulfate or zinc gluconate, while iodine may be added in the form of potassium iodide. It will be appreciated that suitable amounts of additional micronutrients will vary with the micronutrient in question. For example, amounts of about 0.35–0.45 mg of retinyl palmitate per 15 mg of elemental iron, about 5–10 mg of elemental zinc per 15 mg of elemental iron and about 0.25–0.5 mg of iodine per 15 mg of elemental iron may appropriately be added to the present composition.

A method useful to prevent iron deficiency anemia in a mammal is also provided. The method involves the steps of adding a therapeutically effective amount of the present composition to a food, and then administering the food to the mammal requiring treatment. The term "therapeutically effective" as it is used with respect to the present composition refers to an amount which is effective to prevent iron deficiency anemia, or at least minimize the occurrence of adverse effects related thereto, while not exceeding an amount which would be toxic or otherwise harmful. In this regard, precise dosage sizes appropriate to prevent anemia can readily be established in appropriately controlled trials. It is anticipated that an effective treatment regimen will be the administration of a dosage in the range of about 10–25 mg per day, more preferably about 10–17 mg per day. This dosage is applicable for administration to infants and young children, i.e. children between the ages of 2–5 years, as well as being appropriate for administration to older children, i.e. children above 5 years of age, and adults. Administration of larger amounts, for example, 15–34 mg per day may be required by pregnant women.

It will be appreciated that there is no restriction on the foods or beverages to which the present composition can be added. Since the present composition is particularly beneficial for use in the prevention of anemia in infants and young children, the composition will typically be added to foods and beverages generally consumed by infants and young children. Examples of such foods include pureed or semi-solid foods, for example cereals, gruels, porridges, purees of fruit, vegetables, meat or mixtures thereof, as well as milk-based products including, but not strictly limited to, milk, powdered milk, infant formula, puddings, yoghurt, creamed cheese, cottage cheese, and other dairy products which form a part of the diet of infants and young children. The term milk-based products is also meant to include milk substitutes including lactose-free milk and associated products, soy milk and the like.

In another aspect of the present invention, there is provided an article of manufacture including packaging material and a pharmaceutical composition contained within said packaging material which is therapeutically effective to prevent iron deficiency anemia The composition comprises a therapeutically effective amount of micro-encapsulated iron granules in combination with a lipid-based excipient. The packaging may indicate that the composition is effective to prevent iron deficiency anemia, or may indicate that the composition contains iron and ingestion of iron prevents anemia. The packaging may further include directions for use, either in written format or in the form of a series of simple illustrations.

In a preferred embodiment, a single daily dosage of the composition is packaged, for example in a sachet-type package, comprising about 10–17 mg of elemental iron in the form of micro-encapsulated granules and about 400–450 mg of excipient. In a particularly preferred embodiment, the package will additionally include ascorbic acid in an amount of about 40–50 mg.

The present invention is described in more detail by reference to the following specific examples which are not to be construed as limiting.

EXAMPLE 1

Preparation of an iron-containing Composition

Encapsulated ferrous fumarate 60% (1 gram delivers 600 mg ferrous fumarate), having a particle size of no more than about 850 microns in which about 99% of the particles pass through a U.S. No. 20 sieve, was obtained from Watson Foods Co., Inc. (Connecticut).

Ascorbic acid (3.5 kg; obtained from Basf) was thoroughly mixed in a large aluminum bowl with an excipient (25 kg; obtained from New Dundee Creamery, Division of Ault Foods Limited) containing corn syrup solids, hydrogenated vegetable oil and/or hydrogenated coconut oil, sodium caseinate, potassium phosphate di-basic, sodium phosphate di-basic, mono and diglycerides, acetylated tartaric acid esters of monoglycerides, artificial colour, and natural and artificial flavour.

In a 2-stage fill, 65 mg aliquots of encapsulated ferrous fumarate was added to foil-lined sachet packets followed by the addition of 450–500 mg of ascorbic acid/excipient mixture. The sachets were appropriately sealed along their open edge.

Optionally, 2.1 kg zinc gluconate is admixed with the ascorbic acid and excipient. This mixture is then added to ferrous funarate-containing sachets as set out above.

EXAMPLE 2

Relative Bioavailability of Micro-encapsulated iron

The bioavailability of iron in the composition set out in Example 1 has been determined using the hemoglobin-repletion test in rats as follows.

Male weanling Sprague-Dawley rats housed individually in stainless steel cages were fed a low-iron diet and de-ionized distilled water ad lib for 24 days. The low-iron diet contained no more than about 3 mg of iron per kg of diet. Following the 24 day depletion period, approximately 200 µl of blood was drawn from the tail vein of each rat for hemoglobin analysis. Anemic rats having hemoglobin values between 30 and 60 g/L were used in the study. The rats were housed individually in cages in a randomized block design. The rats were divided into groups, each group being fed ad libitum a test diet selected from 0, 10 or 20 mg of one of micro-encapsulated or coated ferrous fumarate (prepared as described in Example 1), micro-encapsulated or coated ferrous fumarate with zinc, uncoated ferrous fumarate particles or uncoated ferrous sulphate (a reference compound determined to have a relative bioavailability of 100) per kilogram of diet. The following chart more specifically sets out the test groups:

| # of Animals | Ferrous Sulfate (Fe—SO4.7H2O) | Coated Ferrous fumarate | Coated Ferrous fumarate + zinc | Ferrous fumarate |
| --- | --- | --- | --- | --- |
| 10 | 0 | 0 | 0 | 0 |
| 10 | 10 mg Fe/kg diet | 0 | 0 | 0 |
| 10 | 20 mg Fe/kg diet | 0 | 0 | 0 |
| 10 | 0 | 10 mg Fe/kg diet | 0 | 0 |
| 10 | 0 | 20 mg Fe/kg diet | 0 | 0 |
| 10 | 0 | 0 | 0 Fe; 10 mg/kg Zn | 0 |
| 10 | 0 | 0 | 10 Fe; 10 mg/kg Zn | 0 |
| 10 | 0 | 0 | 20 Fe; 10 mg/kg Zn | 0 |
| 10 | 0 | 0 | 0 | 10 mg |

-continued

| # of Animals | Ferrous Sulfate (Fe—SO4.7H2O) | Coated Ferrous fumarate | Coated Ferrous fumarate + zinc | Ferrous fumarate |
|---|---|---|---|---|
| 10 | 0 | 0 | 0 | Fe/kg diet 20 mg |
| Total 100 | | | | Fe/kg diet |

The results, as shown in FIG. 1, indicate that hemoglobin response is dependent the amount of iron in the rat's diet. Moreover, there was no significant difference in the hemoglobin response between rats fed similar amounts of iron as the reference compound (ferrous sulfate) versus rats fed micro-encapsulated ferrous fumarate. Referring to FIG. 1, the control group represents rats fed a diet containing no iron, the "low iron" diet represents a diet containing 10 mg micro-encapsulated ferrous fumarate/kg of diet, the "high iron control" diet represents a diet containing 20 mg ferrous sulfate/kg of diet and the "high iron" diet represents a diet containing 20 mg micro-encapsulated ferrous fumarate/kg of diet. There was no change in the hemoglobin of the control after 14 days of feeding, while mean hemoglobin response of the low iron diet group was 18 g/L and the mean hemoglobin response of the high iron control and high iron diet groups was 31 g/L and 33 g/L, respectively.

EXAMPLE 3

Pilot Study to Determine the Efficacy of the Present iron-containing Composition to Prevent Anemia Sixty infants between the ages of 6 and 12 months were recruited into the study following parental consent. The hemoglobin of each infant was determined using a finger prick blood sample. Non-anemic infants were then randomized in a double-blind fashion to receive daily sachets containing a placebo or micro-encapsulated iron composition as prepared in Example 1.

Thirty infants will receive the placebo-sachets for 2 months, and thirty infants will receive the iron-containing sachets for 2 months. At the end of the two month period, the hemoglobin of each infant will be determined by taking a second finger prick blood sample. The difference in the number of anemic infants in each group will be calculated and will indicate the efficacy of the iron-containing composition.

I claim:

1. An article of manufacture consisting essentially of:
   (a) a packaging material; and
   (b) a composition contained within said packaging material, wherein the composition consists essentially of that formed upon admixture of microencapsulated iron granules in combination with an excipient, wherein the excipient is an edible oil in hydrogenated form, and optionally, one or more of a bioavailable form of an additional micronutrient.

2. An article of manufacture of claim 1, wherein the composition consists essentially of: an admixture of microencapsulated iron granules in combination with the excipient, and one or more of a bioavailable form of a compound selected from zinc, vitamin A, iodine and ascorbic acid.

3. An article of manufacture of claim 1, wherein the iron granules are no more than about 850 microns in diameter.

4. An article of manufacture of claim 1, wherein the iron granules are encapsulated with a coating, said coating being prepared from a compound selected from the group consisting of monoglycerides, diglycerides, ethyl cellulose, hydrogenated soy bean oil and mixtures thereof.

5. An article of manufacture of claim 1, wherein the composition contains one or more of a bioavailable form of an additional micronutrient.

6. An article of manufacture of claim 1, wherein the composition contains one or more of a bioavailable form of a compound selected from zinc, vitamin A, iodine and ascorbic acid.

7. An article of manufacture consisting essentially of:
   (a) a packaging material; and
   (b) a composition contained within a sachet, wherein said composition consists essentially of that formed upon admixture of a single daily dose of a therapeutically effective amount of elemental iron as microencapsulated iron granules in combination with an excipient, and optionally, one or more of a bioavailable form of an additional micronutrient.

8. An article of manufacture of claim 7, wherein the composition consists essentially of: an admixture of microencapsulated iron granules in combination with the excipient, and one or more of a bioavailable form of a compound selected from zinc, vitamin A, iodine and ascorbic acid.

9. An article of manufacture of claim 7, wherein the excipient is an edible oil in hydrogenated form.

10. An article of manufacture of claim 7, wherein the iron granules are no more than about 850 microns in diameter.

11. An article of manufacture of claim 7, wherein the iron granules are encapsulated with a coating, said coating being prepared from a compound selected from the group consisting of monoglycerides, diglycerides, ethyl cellulose, hydrogenated soy bean oil and mixtures thereof.

12. An article of manufacture consisting essentially of:
   (a) a packaging material; and
   (b) a composition contained within said packaging material, wherein said composition consists essentially of that formed upon admixture of a single daily dose of a therapeutically effective amount of elemental iron as microencapsulated iron granules in combination with an excipient, and optionally, one or more of a bioavailable form of an additional micronutrient, and wherein:
   (c) the iron granules are encapsulated with a coating selected from the group consisting of monoglycerides, diglycerides, ethyl cellulose, hydrogenated soy bean oil and mixtures thereof; and the excipient is an edible oil in hydrogenated form.

13. An article of manufacture of claim 7, wherein the composition contains one or more of a bioavailable form of an additional micronutrient.

14. An article of manufacture of claim 7, wherein the composition contains one or more of a bioavailable form of a compound selected from zinc, vitamin A, iodine and ascorbic acid.

15. An article of manufacture consisting essentially of:
(a) a packaging material; and
(b) a composition contained within said packaging material, wherein the composition consists essentially of that formed upon admixture of microencapsulated iron granules in combination with a lipid-based excipient, and optionally, one or more of a bioavailable form of an additional micronutrient.

16. An article of manufacture consisting essentially of:
(a) a packaging material; and
(b) a composition contained within said packaging material, wherein the composition consists essentially of that formed upon admixture of microencapsulated iron granules in combination with a lipid-based excipient, and one or more of a bioavailable form of a compound selected from zinc, vitamin A, iodine and ascorbic acid.

17. An article of manufacture of claim 1, wherein said excipient is a lipid-based excipient.

18. An article of manufacture consistent essentially of:
(a) a packaging material; and
(b) a composition contained within said packaging material, wherein the composition consists essentially of that formed upon admixture of microencapsulated iron granules in combination with a lipid-based excipient, and one or more of a bioavailable form of an additional micronutrient.

19. An article of manufacture of claim 7, wherein said excipient is a lipid-based excipient.

20. An article of manufacture consisting essentially of:
(a) a packaging material; and
(b) a composition contained within said packaging material, wherein said composition consists essentially of that formed upon admixture of a single daily dose of a therapeutically effective amount of elemental iron as microencapsulated iron granules in combination with a lipid-based excipient, and one or more of a bioavailable form of a compound selected from zinc, vitamin A, iodine and ascorbic acid.

21. An article of manufacture consisting essentially of:
(a) packaging material; and
b) a composition contained within said packaging material, wherein said composition consists essentially of that formed upon admixture of a single daily dose of a therapeutically effective amount of elemental iron as microencapsulated iron granules in combination with a lipid-based excipient, and one or more of a bioavailable form of an additional micronutrient.

22. An article of manufacture of claim 14, wherein said excipient is a lipid-based excipient.

* * * * *